United States Patent
Rubinstein et al.

[11] Patent Number: 5,885,226
[45] Date of Patent: Mar. 23, 1999

[54] BONE MARROW BIOPSY NEEDLE WITH CUTTING AND/OR RETAINING DEVICE AT DISTAL END

[75] Inventors: Daniel B. Rubinstein, Brookline, Mass.; Alan I. Rubinstein, Los Angeles, Calif.

[73] Assignee: International Medical Technologies Corporation, Los Angeles, Calif.

[21] Appl. No.: 754,197

[22] Filed: Nov. 20, 1996

Related U.S. Application Data

[60] Continuation of Ser. No. 548,588, Oct. 26, 1995, Pat. No. 5,583,628, which is a division of Ser. No. 863,457, Apr. 6, 1992, Pat. No. 5,462,062, which is a continuation-in-part of Ser. No. 806,486, Dec. 13, 1991, abandoned.

[51] Int. Cl.⁶ ................................................. A61B 10/00
[52] U.S. Cl. ........................................... 600/564; 606/167
[58] Field of Search ................................. 600/564, 566, 600/567; 604/277; 606/167, 170, 171

[56] References Cited

U.S. PATENT DOCUMENTS

| | | | |
|---|---|---|---|
| 1,867,624 | 7/1932 | Hoffman | 128/754 |
| 4,649,918 | 3/1987 | Pegg et al. | 128/754 |
| 4,903,709 | 2/1990 | Skinner | 600/567 |

FOREIGN PATENT DOCUMENTS 1604361  11/1990  U.S.S.R. ................. 128/754

*Primary Examiner*—Max Hindenburg
*Assistant Examiner*—Pamela Wingood
*Attorney, Agent, or Firm*—Ostrolenk, Faber, Gerb & Soffen, LLP

[57] ABSTRACT

A bone marrow biopsy needle provided with blades which cut and retain a biopsy core. In one embodiment, the cutting blades of the needle are hinged at the distal end of the needle and are mechanically coupled to an actuator at the proximal end of the needle. The needle is preferably formed with inner and outer walls to provide a space therebetween for the mechanical coupling. The cutting blades are retained in a dead space against the outer wall of the needle when the needle is open. In lieu of a hinged arrangement, the outer wall of the needle may be tapered at its distal end so that the blades are forced together when they are pushed forward. In another embodiment, the cutting blades are pre-curved inward, but are retained against the inner surface of the needle wall until pushed forward. In yet another embodiment, the distal ends of the cutting blades rest within a curved circumferential recess provided in the needle wall, and, when pushed forward, move together to cut and retain the biopsy core.

4 Claims, 4 Drawing Sheets

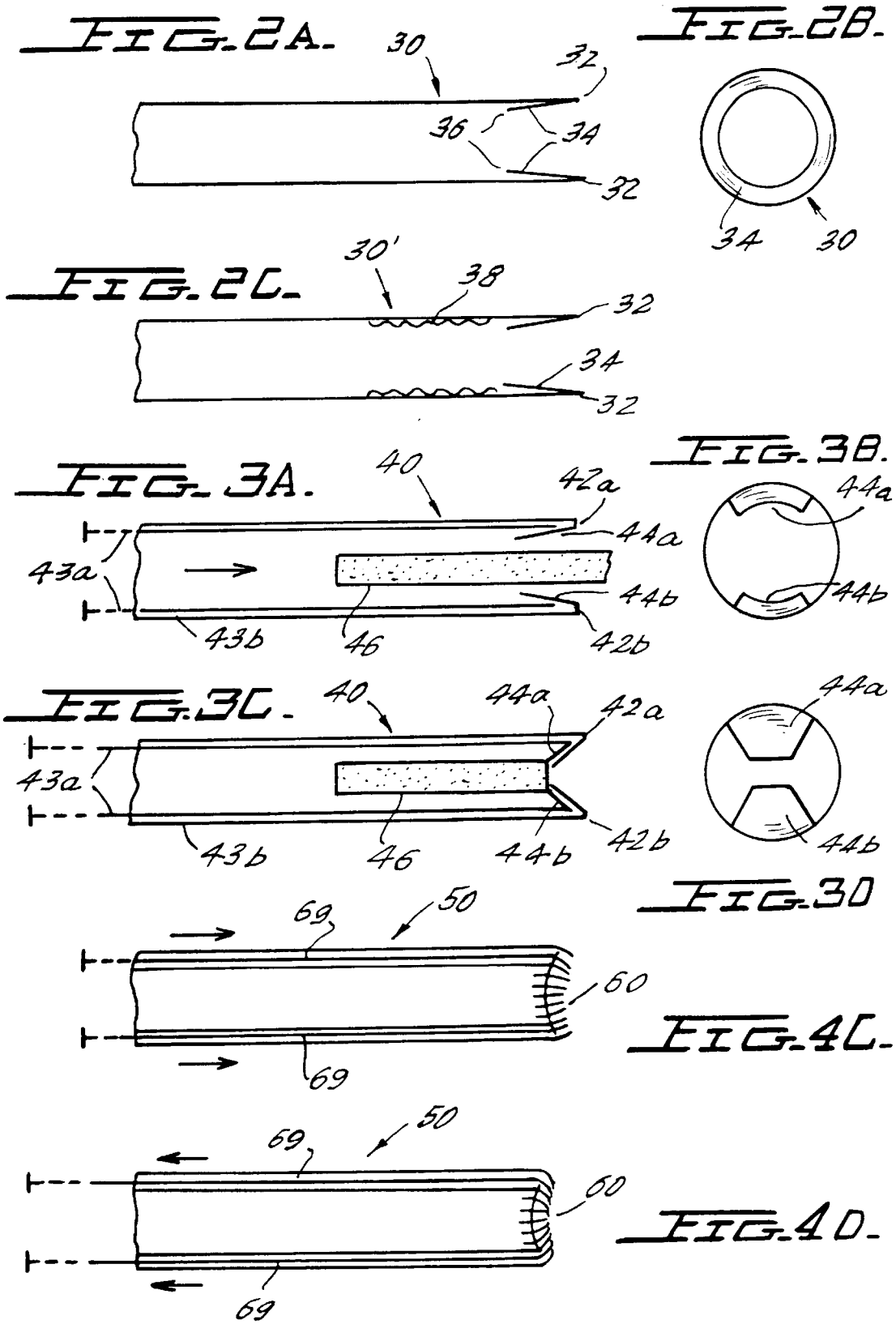

BONE MARROW BIOPSY NEEDLE WITH CUTTING AND/OR RETAINING DEVICE AT DISTAL END

This is a continuation of application Ser. No. 08/548,588, filed on Oct. 26, 1995, now U.S. Pat. No. 5,583,628, which is a division of application Ser. No. 07/863,457, filed Apr. 6, 1992, now U.S. Pat. No. 5,462,062, which is a continuation-in-part application of Ser. No. 07/806,486, filed on Dec. 13, 1991, now abandoned.

BACKGROUND OF THE INVENTION

When a bone marrow biopsy is performed, a biopsy core, which consists of a plug of bone and marrow, is withdrawn with a bone marrow biopsy needle from the body of the patient. At times, it is difficult to retain the biopsy core in the needle while the needle is being withdrawn from the patient.

FIG. 1 is a schematic cross-sectional view of the known Jamshidi® bone marrow biopsy needle, which is available from Baxter Healthcare Corp. A cylindrical needle 20 tapers slightly at the distal end 22 to form a narrowed tip. An inner trocar or introducer 24 must be inserted and securely retained in the needle 20 during insertion into the patient. The trocar 24 has a chisel-like tip 26 which aids the needle to penetrate the patient's bone. After the bone is pierced, the trocar is removed rearwards from the needle and insertion of the needle continues in order to collect the desired biopsy core within the needle. Because of the inward curve of the end 22, the needle 20 has a cylindrical "dead space" 28, which is not usable to contain the biopsy core.

With the Jamshidi® needle, it is difficult to keep the solid biopsy material in the needle as the operator is withdrawing the needle from the patient. A biopsy core approximately 1½ inches (3.8 mm) is generally needed. Conventionally, it is necessary to shake the needle from side to side, to break the biopsy core loose from the adjacent marrow. This agitation of the bone marrow is uncomfortable for the patient. It also may create a risk of metastasizing malignant cancer, leukemia, or lymphoma cells which are infiltrated in the marrow of the patient, because the bone marrow is highly vascular. The marrow contains a vascular system which is quite complex and includes a vascular sinusoidal system. See Wintrobe, M. M., et al., eds., *Clinical Hematology* (Lea & Febiger 1981); Anat. Rec. 68:55 (1970); and Weiss, L.,"Histopathology of the Bone Marrow," in *Regulation of Hematopoiesis*, A. S. Gordon, ed., (Appleton-Century Crafts 1970).

Therefore, it would be desirable to provide some means of separating or cutting the biopsy core from the surrounding marrow in order to free it for removal, without unnecessary agitation of the marrow. Such a device would be effective to reduce or eliminate risk and discomfort for the patient.

Another problem with the prior art needle is that, even after the biopsy core is broken loose from the bone marrow, it sometimes falls out of the needle as the needle is being withdrawn from the patient's body. Thus, there is a need for a biopsy needle having a closable distal end for retaining the biopsy core in the needle.

SUMMARY OF THE INVENTION

Accordingly, an object of the present invention is to provide a bone marrow biopsy needle with a device at the distal end of the needle that can be actuated by the operator at the proximal end of the needle, for cutting off the biopsy core from the adjacent marrow, before it is withdrawn from the patient.

Another object is to provide a device for retaining the biopsy core within the needle as the needle is withdrawn from the patient, such as a device for closing the distal end, or another type of retaining device.

With the invention, it is no longer necessary to shake the needle before withdrawal in order to break loose the biopsy core from the underlying marrow, and the core is reliably retained in the needle during withdrawal. Discomfort and risk to the patient are substantially reduced or eliminated.

Thus, the disclosed embodiments of the invention are a marked improvement over all previous needles, including the Jamshidi® and Jamshidi-type needles, and the Gardner, Silverman, Bierman, Conrad, Crosby, Westerman-Jensen and Osgood types of needles.

Other features and advantages of the present invention will become apparent from the following description of the invention which refers to the accompanying drawings.

BRIEF DESCRIPTION OF THE DRAWINGS

FIGS. 2A and 2B are respectively a schematic cross-section and an end view showing a first embodiment of the invention;

FIG. 2C is a schematic cross-section showing a modification of the foregoing embodiment;

FIGS. 3A and 3B are, respectively, a schematic cross-section and an end view showing a second embodiment of the invention in the open position, and FIGS. 3C and 3D show the second embodiment in a closed position;

FIGS. 4C and 4D are schematic cross-sectional views showing the third embodiment provided with a wire arrangement for closing the blades of the needle;

DESCRIPTION OF EMBODIMENTS OF THE INVENTION

Figure 1:
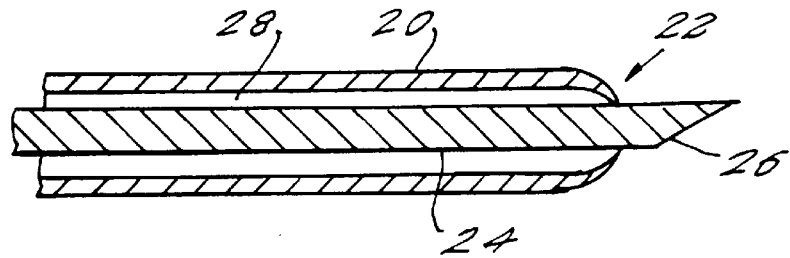
FIG. 1 is a schematic cross-sectional view of the known Jamshidi® bone marrow biopsy needle which is available from Baxter Healthcare Corp.

Referring to FIGS. 2A and 2B, a first embodiment of the invention is illustrated, in which a needle 30 is provided with a sharp cutting edge 32 at its distal end, the needle being turned back inward from the distal end to form an inner "cuff" or flange 34 with a sharp, inwardly directed edge 36. The inwardly directed, angled flange 34 is substantially immobile and helps to retain the biopsy core in the needle. Also, the inner edge 36 helps to cut off the biopsy core with only a slight amount of horizontal and/or vertical movement of the needle.

FIG. 2C shows a variation on the foregoing embodiment, wherein, in addition to the flange 34, the needle 30' has a roughened or toothed region 38 just behind the flange 34 which improves the retention of the biopsy core in place while it is being cut by the edge 36 and then withdrawn.

FIGS. 3A and 3B show, respectively, a schematic cross-section and an end view of a second embodiment of the invention. A needle 40 has a pair of opposed hinges 42a, 42b at its distal end, and a pair of sharp-edged blades 44a an 44b are attached to the hinges at opposite sides of the distal end of the needle. As it is inserted into the patient, the biopsy needle 40 receives the biopsy core 46. Then, as the needle is being removed from the patient, as shown in FIGS. 3C and 3D, as soon as the needle is pulled slightly outward, the biopsy core 46 engages the sharp inner edges of the blades 44a and 44b, thereby closing the blades in order to both cut off the biopsy core and retain it in the needle.

As shown in FIGS. 3A and 3C, a pair of actuating wires 43a and 43b, attached to the blade mechanism, can be provided within needle 40. When wires 43a and 43b are pulled, blades 44a and 44b close, thereby cutting the biopsy and retaining it in place within the needle.

Although the embodiment of FIGS. 3A–3D has two opposed blades, one blade, or a larger number of blades, can be used. For example, the needle can have an iris arrangement of blades, similar to that disclosed below in connection with FIGS. 4A and 4B.

Figure 4A:
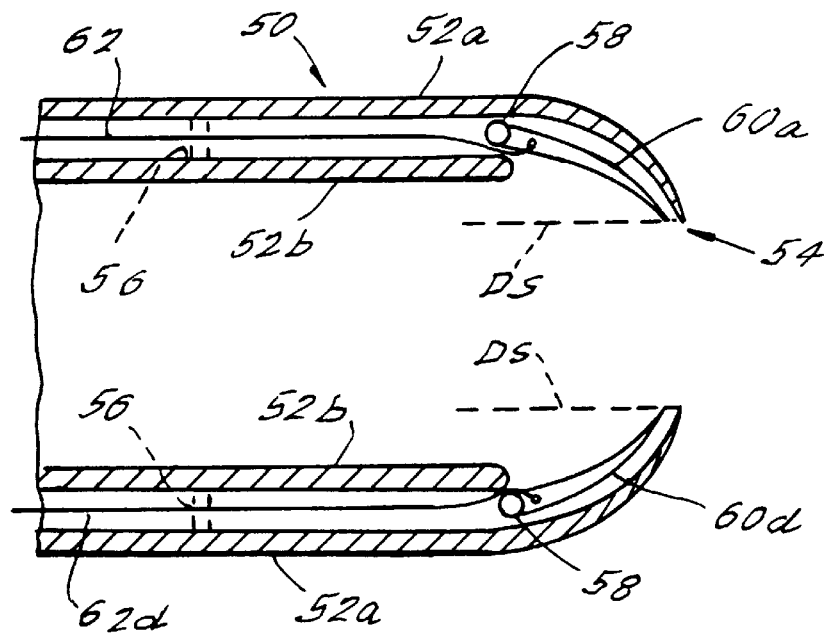
FIG. 4A is a schematic cross-sectional view and FIG. 4B is an end view, showing a third embodiment of the invention, wherein the relative dimensions and arrangement of the parts are greatly expanded for clarity.
Figure 4B:
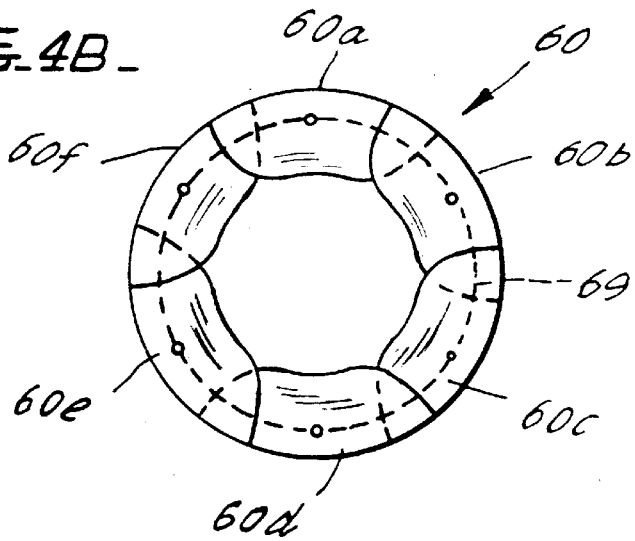

FIG. 4A is a cross-sectional view showing a third embodiment of the invention, wherein the relative dimensions and arrangement of the parts are greatly expanded for clarity. In this embodiment, a needle 50 is provided with an outer cylindrical wall 52a and an inner cylindrical wall 54b. The wall 52a tapers at the distal end of the needle and curves inward to a sharp circular tip edge 54. The walls 52a and 52b are held together, for example, by radial spacers 56, two of these being shown schematically in FIG. 4A. The inner wall 52b ends short of the distal end of the needle and does not substantially curve inward. Near the end of the wall 52b is a series of hinges 58 (six in this embodiment) extending circumferentially around the interior of the needle substantially between the walls 52a and 52b. Attached to the hinges 58 are a series of six blades 60a–60f, which form an iris arrangement as shown in FIG. 4B. Blades 60a–60f have sharp distal edges.

As shown in FIG. 4A, in their initial position, the blades are located completely within the cylindrical "dead space" of the outer wall 52a as indicated by the dotted line DS. Therefore, when the needle is inserted into the bone marrow, the iris 60 presents no obstruction to the entry of the marrow core. When the needle has been inserted and the biopsy is ready to be withdrawn, the blades of the iris 60 are then closed by respective wires attached to the blades 60a–60f, which are pulled by an appropriate pulling device at the proximal end of the needle (not shown). In FIG. 4A, only wires 62a and 62d are shown. The blades of the iris close, cutting off the distal end of the biopsy core and also helping to retain it within the needle 50.

In an alternate embodiment, shown in dashed lines in FIG. 4B, one or more wires may be threaded over the outside of the hinges 58, being guided essentially axially over the hinges. Then, each wire is guided through a guide loop or the like at the inner edge of one blade, or several blades, and is secured near the inner edge of a last one of the blades. In this embodiment, pulling on the wires closes the blades and cuts off and secures the biopsy core. Alternatively, the wire-threading arrangement shown in FIGS. 4C and 4D can be used, in which one wire 69 extends circumferentially around the iris 60, joining all the blades 60a–60f. Wire 69, when pulled, acts simultaneously on all the blades to close the iris.

Instead of employing wires which pull on the blades in order to close them, the blades may alternatively be closed by rods or the like which push on portions of the blades. Further, a detent mechanism (described below in connection with FIGS. 5A and 5C) may be employed to guide the operator as to how far the rods should be pushed in, and to maintain the rods in position.

Figure 5A:
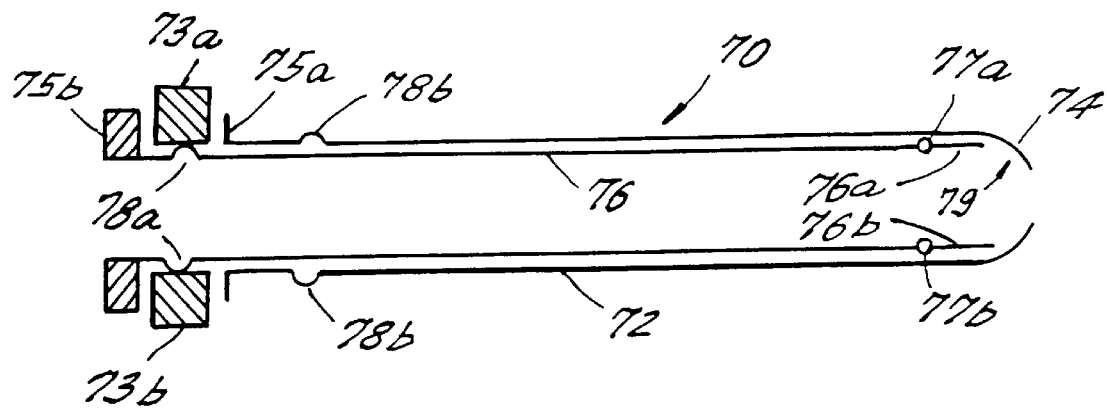
FIGS. 5A and 5C are schematic cross-sectional views, respectively, showing an open and a closed position of a fourth embodiment of the invention.
Figure 5B:
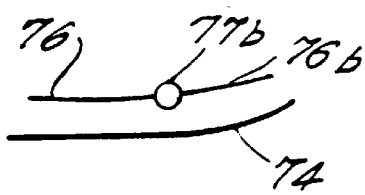
FIG. 5B is cross-sectional detail of a hinge which is usable in the fourth embodiment.
Figure 5D:
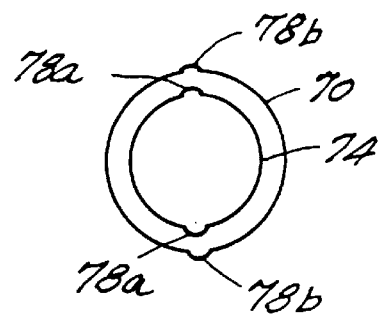
FIGS. 5D and 5E are corresponding end views.

FIGS. 5A and 5B show a fourth embodiment of the invention in which a biopsy needle 70 includes an outer tube 72 with an inwardly tapered end 74, and an inner tube 76 with a pair of opposed blades 76a, 76b which are hinged to the inner tube 76 by hinges 77a, 77b at its distal end. The inner tube 76 is slidable axially within the outer tube 72. The outer and inner tubes 72, 76 have respective operating flanges 75a, 75b at their proximal ends.

While inserting the needle 70 into the patient, the operator presses on the operating flange 75b. The flanges 75a, 75b are separated by two or more blocks 73a, 73b to keep the inner tube from sliding into the outer tube. Then, when the biopsy core has entered the needle, the blocks 73a, 73b are removed and the inner tube 76 is pressed axially into the outer tube 72. The blades 76a, 76b engage the tapered end 74 and are directed radially inward, as shown in FIG. 5C, thereby simultaneously cutting off the biopsy core and retaining it in the needle 70.

Figure 5C:
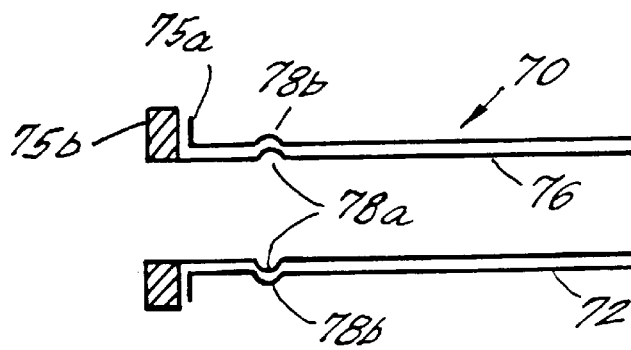
Figure 5E:
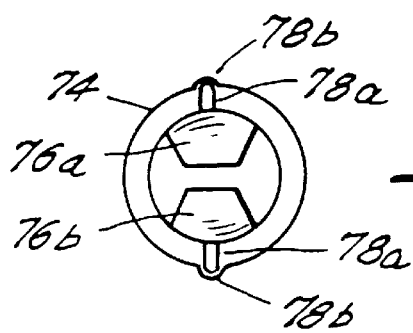

The needle 70 can optionally include a detent arrangement 78, shown in FIG. 5C, in which a small, outwardly curved segment or bulb 78a is provided on the inner tube 76 and a recess 78b of the same shape is provided on the outer tube 72. When the bulb 78a enters the recess 78b, it clicks in place, signalling the operator that the inner tube 76 has been pushed the proper distance into the outer tube 72, and helping to maintain the relative position of the inner and outer tubes 72, 76. To remove the biopsy (after the needle has been withdrawn from the patient), the operator squeezes operating flange 75, thereby releasing bulb 78a from recess 78b, allowing the inner tube to be slid back, opening blades 76a and 76b.

Figure 6A:
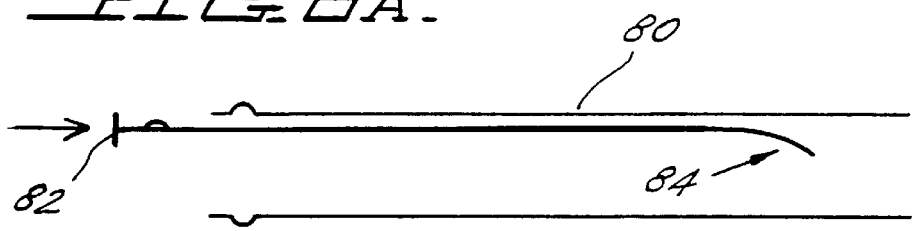
FIGS. 6A and 6B are schematic cross-sections of a fifth embodiment of the invention, in open and closed positions, respectively.
Figure 6B:
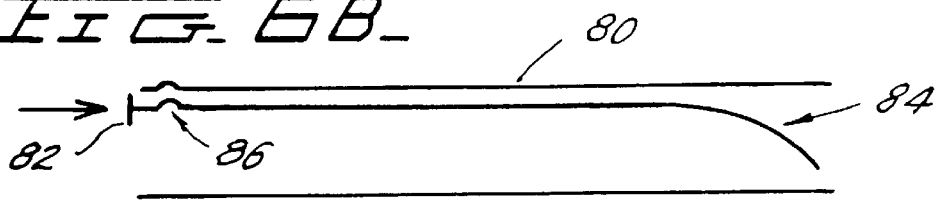

FIGS. 6A and 6B are schematic cross-sections illustrating a fifth embodiment of the invention, in which a needle 80 is provided with a distal, pre-curved metal blade 84 actuated by a proximal knob 82. Pre-curved metal blade 84 is sufficiently flexible to be held in place against the inner surface of needle 80 by very small clips (not shown). When blade 84 is moved inward by pushing on proximal knob 82, its distal end moves beyond the clips and is no longer held against the inside of needle 80. Since blade 84 is pre-curved, it moves inward as shown in FIG. 6B, cutting the biopsy sample and closing the entrance to the needle, thereby preventing the biopsy from falling back out of the needle 80. Since the blade 84 is initially held parallel and close to the inner wall of the needle 80 by the clips, biopsy material cannot become lodged between the blade 84 and the needle wall 80 when the biopsy is entering the needle. As shown in FIG. 6B, a detent arrangement 86 can be used in the same manner as in the previous embodiments to signal the operator when the blade is in the correct fully inserted position and to maintain the blade in that position.

Figure 7A:
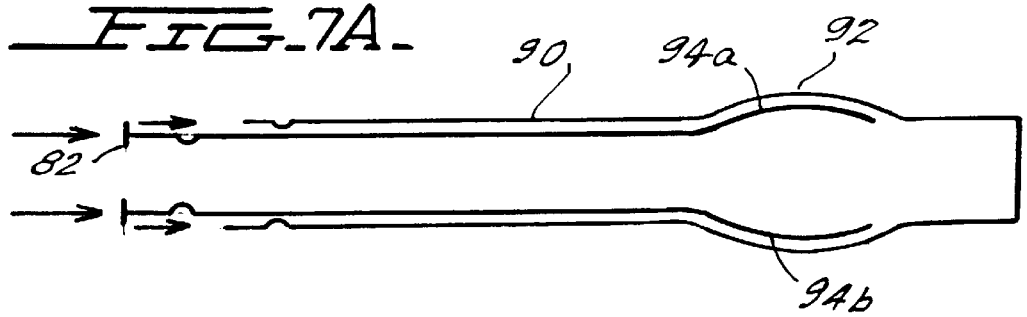
FIGS. 7A and 7B are schematic cross-sections.
Figure 7C:
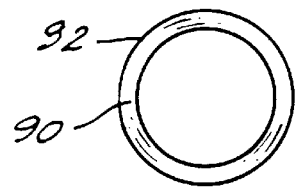
FIGS. 7C and 7D are end views, of a sixth embodiment of the invention, in open and closed positions, respectively.
Figure 7B:
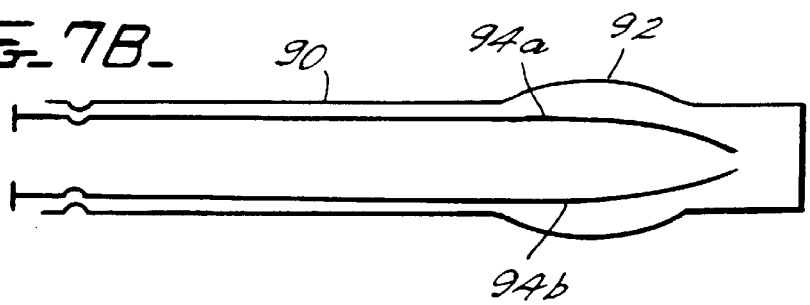
Figure 7D:
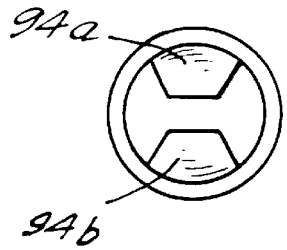

FIGS. 7A and 7B are schematic cross-sections, and FIGS. 7C and 7D are end views, of a sixth embodiment of the invention, in which a pair of pre-curved blades 94a and 94b are fit into a curved circumferential recess 92 in the needle 90. After the biopsy is inside the needle 90, the blades 94a and 94b are advanced, cutting the biopsy and retaining it in place. The blades 94a and 94b are pre-curved at an angle so as to meet each other when pushed forward. Since the needle 90 need only be inserted into the patient up to, but not including, the recess 92, the "bulged" portion of the needle never enters the patient; thus, there is no "wider hole" or extra discomfort to the patient. As before, the needle 90 can be provided with a detent arrangement to ensure that the blades 94a and 94b are advanced to the proper position.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. In a bone marrow biopsy needle comprising a tube which extends from a proximal end to a distal end and having an opening at the distal end for receiving a biopsy core when the needle is inserted by an operator into the bone marrow of a patient, the improvement comprising an annular cutting means attached to the interior of said tube and extending about the tube at the distal end and operable for cutting the biopsy core from the bone marrow while the biopsy needle is present in the bone marrow, wherein the cutting means includes an inner flange which extends from the distal end toward the proximal end of the tube and has a sharpened cutting edge at a proximal end of the flange.

2. A needle in claim 1, further comprising a sharpened cutting edge at the distal end of the needle.

3. A needle as in claim 1, wherein the inner flange is attached to the tube at the distal opening.

4. A needle as in claim 1, further comprising gripping means on an inner wall of the tube and spaced from the distal end, for gripping the biopsy core.

* * * * *